United States Statutory Invention Registration [19]

[11] Reg. Number: H734

Sudilovsky [43] Published: Feb. 6, 1990

[54] METHOD FOR INHIBITING ONSET OF OR TREATING MIGRAINE HEADACHES EMPLOYING AN ACE INHIBITOR

[75] Inventor: Abraham Sudilovsky, Lawrenceville, N.J.

[73] Assignee: E. R. Squibb & Sons, Inc., Princeton, N.J.

[21] Appl. No.: 164,689

[22] Filed: Mar. 7, 1988

Related U.S. Application Data

[63] Continuation-in-part of Ser. No. 118,131, Nov. 9, 1987, abandoned.

[51] Int. Cl.[4] ..... A61K 37/00; A61K 31/44

[52] U.S. Cl. ..... 514/19; 514/2; 514/21; 514/289; 514/291; 514/295; 514/338; 514/339; 548/413

[58] Field of Search ..... 514/2, 19, 21, 289, 514/291, 295, 338, 339; 548/413

[56] References Cited

U.S. PATENT DOCUMENTS

| | | | |
|---|---|---|---|
| 4,374,829 | 2/1983 | Harris et al. | 514/21 |
| 4,432,971 | 2/1984 | Karanewsky et al. | 548/413 |
| 4,472,380 | 9/1984 | Harris et al. | 514/2 |
| 4,548,941 | 10/1985 | Halczenko et al. | 514/295 |
| 4,579,851 | 4/1986 | Claremon | 514/291 |
| 4,587,253 | 5/1986 | Halczenko et al. | 514/289 |
| 4,591,587 | 5/1986 | Remy | 514/228.5 |
| 4,599,341 | 7/1986 | Halczenko et al. | 514/282 |
| 4,634,716 | 1/1987 | Parsons et al. | 514/338 |
| 4,675,321 | 6/1987 | Baldwin et al. | 514/274 |
| 4,711,893 | 12/1987 | Hausberg et al. | 514/339 |

*Primary Examiner*—John F. Terapane
*Assistant Examiner*—Daniel S. Metzmaier
*Attorney, Agent, or Firm*—Burton Rodney

[57] ABSTRACT

A method is provided for inhibiting onset of or treating migraine headache by administering an ACE inhibitor, such as captopril, alone or in combination with a calcium channel blocker such as diltiazem or nifedipine, over a prolonged period of treatment.

16 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR INHIBITING ONSET OF OR TREATING MIGRAINE HEADACHES EMPLOYING AN ACE INHIBITOR

REFERENCE TO OTHER APPLICATIONS

This is a continuation-in-part of application Ser. No. 118,131, filed Nov. 9, 1987 now abandoned.

FIELD OF THE INVENTION

The present invention relates to a method for inhibiting onset of or treating migraine headaches by administering an ACE inhibitor, such as captopril, zofenopril, fosinopril or enalapril, alone or in combination with a calcium channel blocker, such as diltiazem or nifedipine.

BACKGROUND OF THE INVENTION

U.S. Pat. Nos. 4,046,889 and 4,105,776 to Ondetti et al discloses proline derivatives which are angiotensin converting enzyme (ACE) inhibitors and have the general formula

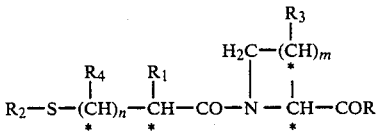

wherein

R is hydroxy, $NH_2$ or lower alkoxy;

$R_1$ and $R_4$ each is hydrogen, lower alkyl, phenyl or phenyl-lower alkyl;

$R_2$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoyl-amidomethyl,

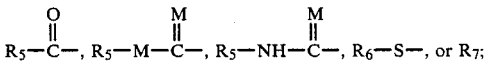

$R_3$ is hydrogen, hydroxy or lower alkyl;

$R_5$ is lower alkyl, phenyl or phenyl-lower alkyl;

$R_6$ is lower alkyl, phenyl, substituted phenyl (wherein the phenyl substituent is halo, lower alkyl or lower alkoxy), hydroxy-lower alkyl or amino(carboxy)lower alkyl;

$R_7$ is

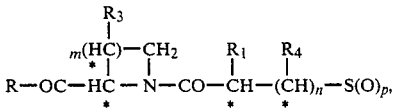

M is O or S; m is 1 to 3; n and p each is 0 to 2.

The asterisks indicate asymmetric carbon atoms. Each of the carbons bearing a substituent $R_1$, $R_3$ and $R_4$ is asymmetric when that substituent is other than hydrogen.

These patents disclose captopril.

U.S. Pat. No, 4,168,267 to Petrillo discloses phosphinylalkanoyl prolines which have the formula

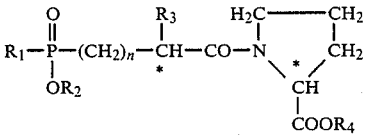

wherein $R_1$ is lower alkyl, phenyl or phenyl-lower alkyl;

$R_2$ is hydrogen, phenyl-lower alkyl or a metal ion;

$R_3$ is hydrogen or lower alkyl;

$R_4$ is hydrogen, lower alkyl, phenyl-lower alkyl or a metal ion; and n is 0 or 1.

U.S. Pat. No. 4,337,201 to Petrillo discloses phosphinylalkanoyl substituted prolines having the formula

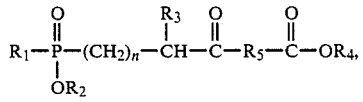

or a salt thereof, wherein $R_1$ is alkyl, aryl, arylalkyl, cycloalkyl, or cycloalkylalkyl; one of $R_2$ and $R_4$ is

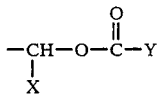

and the other is hydrogen, alkyl aryalkyl or

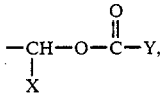

wherein X is hydrogen, alkyl or phenyl and Y is hydrogen, alkyl, phenyl or alkoxy, or together X and Y are $-(CH_2)_2-$, $-(CH_2)_3-$, $-CH=CH-$ or

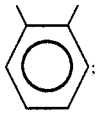

$R_3$ is hydrogen or alkyl;

$-R_5-COOR_4$ is

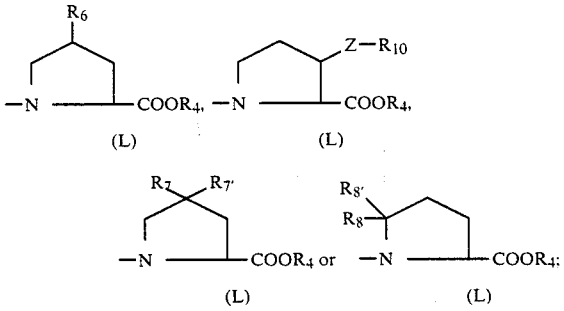

$R_6$ is hydrogen, hydroxy, alkyl, halogen, azido, amino, cycloalkyl, aryl, arylalkyl, carbamoyloxy, N,N-dialkylcarbamoyloxy, or —Z—R9;

$R_7$ and $R'_7$ are the same and each is halogen or —Z—$R_{10}$, or $R_7$ and $R'_7$ together are =O, —O—$(CH_2)_m$—O—or —S—$(CH_2)_m$—S—;

$R_8$ is hydrogen and $R'_8$ is phenyl, 2-hydroxyphenyl or 4-hydroxyphenyl or $R_8$ and $R'_8$ together are=O;

$R_9$ is alkyl, aryl, arylalkyl, 1— or 2-naphthyl, or biphenyl;

$R_{10}$ is alkyl, aryl or arylalkyl;

Z is oxygen or sulfur;

n is 0 or 1; and m is 1 or 2.

The Petrillo patent covers fosinopril

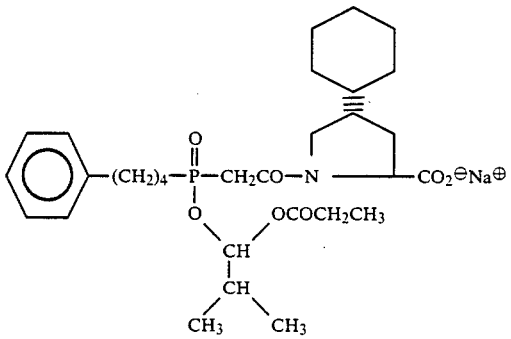

U.S. Pat. No. 4,432,971 to Karanewsky et al discloses phosphonamidate substituted amino or imino acids which are angiotensin converting enzyme inhibitors and salts thereof and have the formula

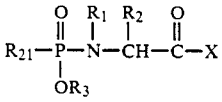

wherein X is an imino or amino acid of the formula

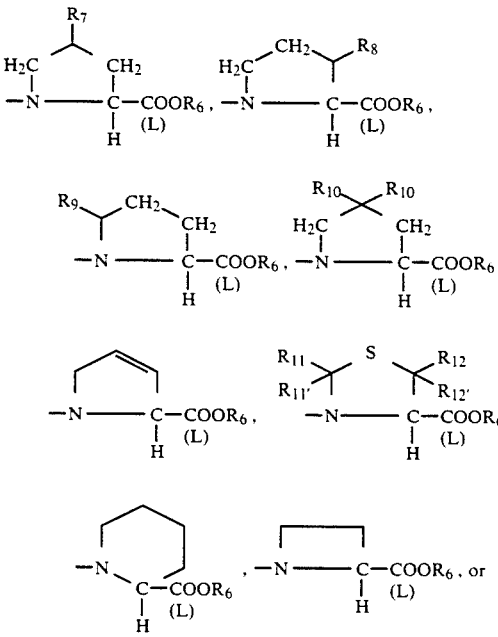

-continued

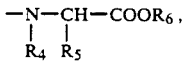

$R_7$ is hydrogen, lower alkyl, halogen, keto, hydroxy,

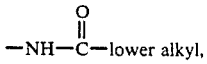

azido, amino,

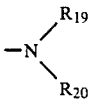

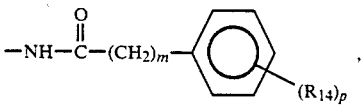

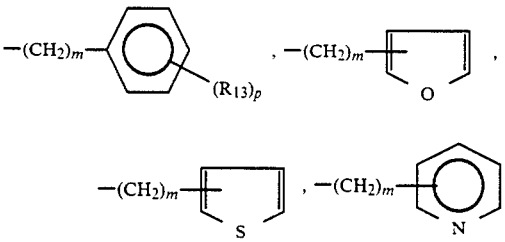

a 1- or 2-naphthyl of the formula

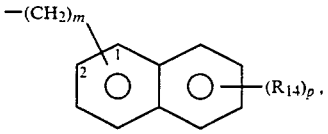

$—(CH_2)_m$-cycloalkyl,

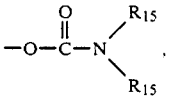

—O-lower alkyl,

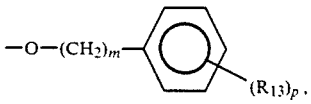

a 1- or 2-naphthyloxy of the formula

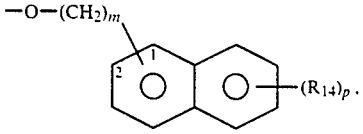

—S-lower alkyl,

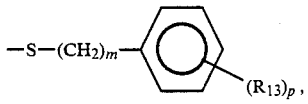

or a 1- or 2-naphthylthio of the formula

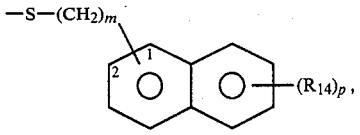

$R_8$ is keto, halogen,

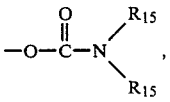

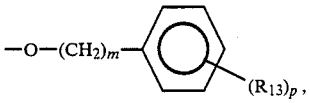

—O-lower alkyl, a 1- or 2-naphthyloxy of the formula

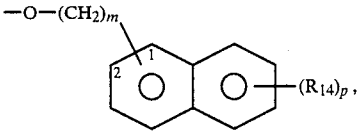

—S-lower alkyl,

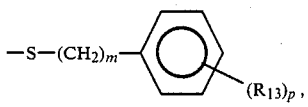

or a 1- or 2-naphthylthio of the formula

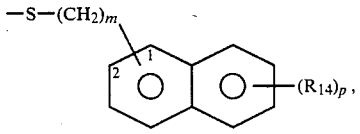

$R_9$ is keto or

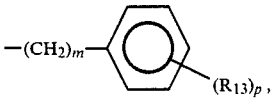

$R_{10}$ is halogen or —Y—$R_{16}$, $R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

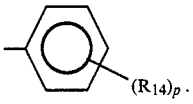

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one, two or three.

p is one, two or three provided that p is more than one only if $R_{13}$ or $R_{14}$ is hydrogen, methyl, methoxy, chloro or fluoro.

$R_{15}$ is hydrogen or lower alkyl of 1 to 4 carbons.

Y is oxygen or sulfur.

$R_{16}$ is lower alkyl of 1 to 4 carbons,

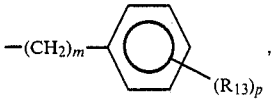

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is hydrogen, lower alkyl, cycloalkyl, or

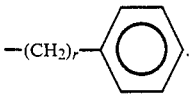

$R_5$ is hydrogen, lower alkyl,

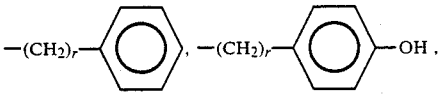

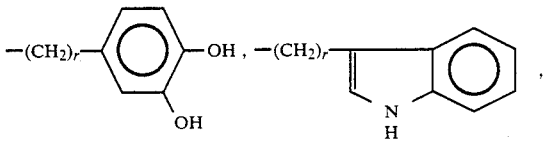

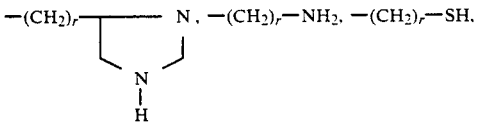

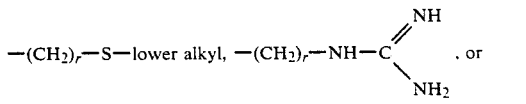

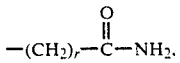

r is an integer from 1 to 4, $R_1$ is hydrogen, lower alkyl or cycloalkyl.

$R_2$ is hydrogen, lower alkyl, halo substituted lower alkyl,

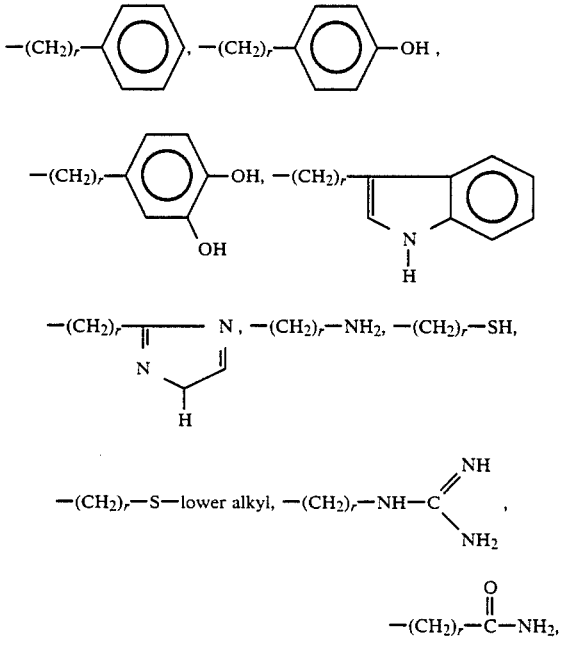

or $R_1$ and $R_2$ taken together are $-(CH_2)_n-$ wherein n is an integer from 2 or 4.

$R_3$ and $R_6$ are independently selected from hydrogen, lower alkyl, benzyl, benzhydryl, or

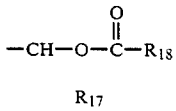

wherein $R_{17}$ is hydrogen, lower alkyl, or phenyl, and $R_{18}$ is hydrogen, lower alkyl, lower alkoxy, phenyl, or $R_{17}$ and $R_{18}$ taken together are $-(CH_2)_2-$, $-(CH_2)_3-$, $-CH=CH-$, or

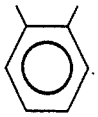

$R_{19}$ is lower alkyl, benzyl, or phenethyl.

$R_{20}$ is hydrogen, lower alkyl, benzyl or phenethyl.

$R_{21}$ is alkyl of 1 to 10 carbons,

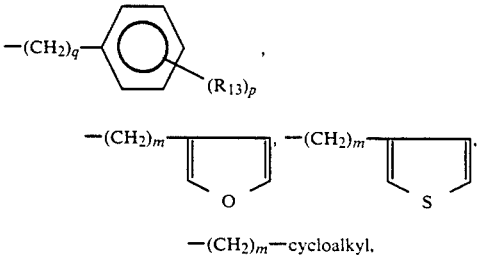

-continued

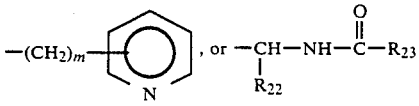

wherein q is zero or an integer from 1 to 7 and $R_{14}$, p and m are as defined above.

$R_{22}$ and $R_{23}$ are independently selected from hydrogen, lower alkyl, halo substituted lower alkyl,

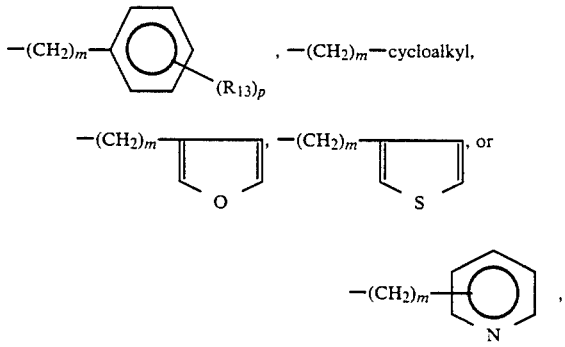

wherein m, $R_{14}$, and p are as defined above.

U.S. Pat. No. 4,374,829 discloses carboxyalkyl dipeptide derivatives which are said to be angiotensin converting enzyme inhibitors and have the formula

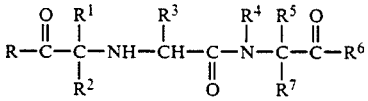

wherein R and $R^6$ are the same or different and are hydroxy, lower alkoxy, lower alkenoxy, dilower alkylamino lower alkoxy (dimethylaminoethoxy), acylamino lower alkoxy (acetylamino-ethoxy), acyloxy lower alkoxy (pivaloyloxymethoxy), aryloxy, such as phenoxy, aryllowerlkoxy, such as benzyloxy, substituted aryloxy or substituted aryllowerlkoxy wherein the substituent is methyl, halo, methoxy, amino, loweralkylamino, diloweralkylamino, hydroxyamino, aryllowerlkylamino such as benzylamino;

$R^1$ is hydrogen, alkyl of from 1 to 20 carbon atoms which include branched and cyclic and unsaturated (such as allyl) alkyl groups, substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxamido, carboloweralkoxy, aryl such as phenyl or naphthyl, substituted aryl such as phenyl wherein the substituent is lower alkyl, lower alkoxy or halo, aryllowerlkyl, aryllowerlkenyl, heteroaryllower alkyl or heteroaryllower alkenyl such as benzyl, styryl or indolyl ethyl, substituted aryllowerlkyl, substituted aryllowerlkenyl, substituted heteroaryllower alkyl, or substituted heteroaryllower alkenyl, wherein the substituents(s) is halo, dihalo, lower alkyl, hydroxy, lower alkoxy, amino, aminomethyl, acylamino (acetylamino or benzoylamino) diloweralkylamino, loweralkylamino, carboxyl, halolowerlkyl, cyano or sulfonamido; aryllowerlkyl or heteroaryllowerlkyl substituted on the alkyl portion by amino or acylamino (acetylamino or benzoylamino);

$R^2$ and $R^7$ are the same or different and are hydrogen or lower alkyl;

$R^3$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, guanidino lower alkyl, imidazolyl lower alkyl, indolyl lower alkyl, mercapto lower alkyl, lower alkylthio lower alkyl;

$R^4$ is hydrogen or lower alkyl;

$R^5$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkylthio lower alkyl;

$R^4$ and $R^5$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, lower alkyl or dilower alkyl;

and the pharmaceutically acceptable salts thereof.

Example 41 of U.S. Pat. No. 4,374,829 describes the preparation of N-(1-ethoxycarbonyl-3-phenylpropyl)-L-alanyl-L-proline.

U.S. Pat. No. 4,452,790 to Karanewsky et al is directed to phosphonate substituted amino or imino acids and salts thereof having the formula

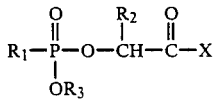

wherein X is an imino or amino acid of the formula

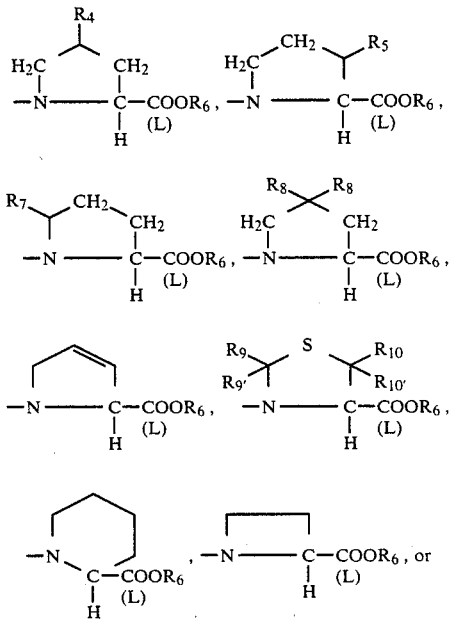

-continued

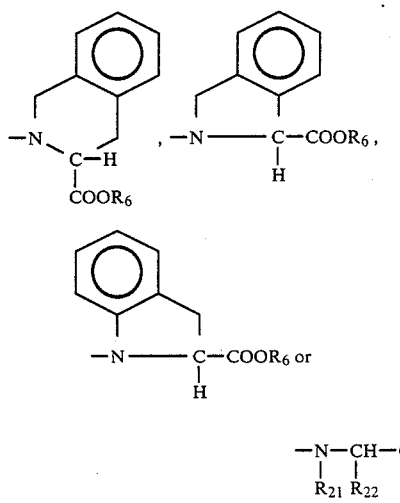

$R_4$ is hydrogen, lower alkyl, halogen, keto, hydroxy,

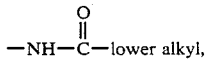

azido, amino,

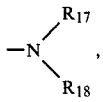

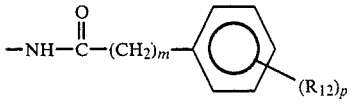

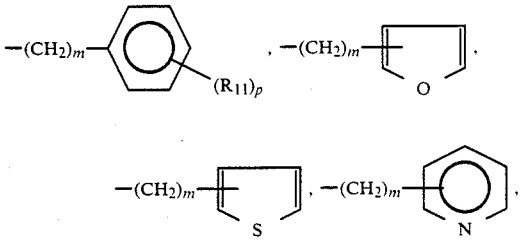

a 1- or 2-naphthyl of the formula

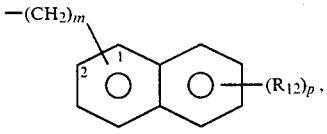

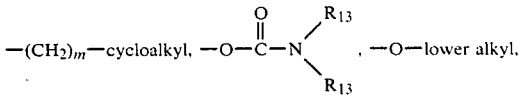

-continued

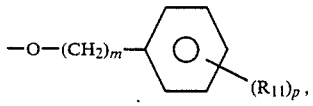

a 1- or 2-naphthyloxy of the formula

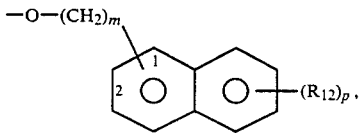

—S—lower alkyl,

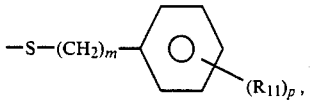

or a 1- or 2-naphthylthio of the formula

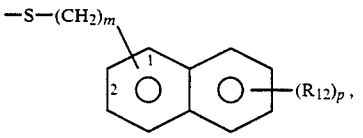

$R_5$ is keto, halogen, $-O-\overset{O}{\overset{\|}{C}}-N\begin{matrix}R_{13}\\R_{13}\end{matrix}$, $R_5$ is keto, halogen,

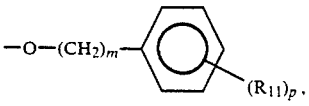

—O-lower alkyl, a 1- or 2-naphthyloxy of the formula

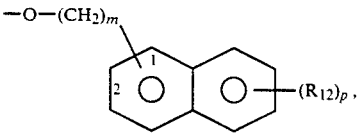

—S-lower alkyl,

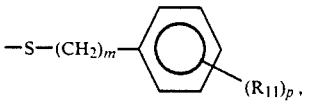

or a 1- or 2-naphthylthio of the formula

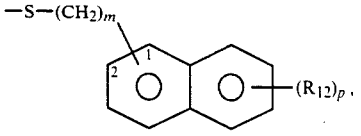

$R_7$ is keto or

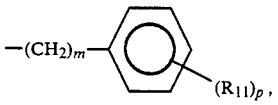

Each $R_8$ is independently halogen or —Y—$R_{14}$.

$R_9$, $R_9'$, $R_{12}$ and $R_{10}'$ are independently selected from hydrogen and lower alkyl or $R_9'$, $R_{10}$ and $R_{10}'$, are hydrogen and $R_9$ is

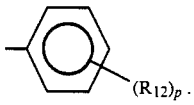

$R_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{12}$ is hydrogen, lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one, two or three.

p is one, two or three provided that p is more than one only if $R_{11}$ or $R_{12}$ is hydrogen, methyl, methoxy, chloro or fluoro.

$R_{13}$ is hydrogen or lower alkyl of 1 to 4 carbons.

Y is oxygen or sulfur.

$R_{14}$ is lower alkyl of 1 to 4 carbons,

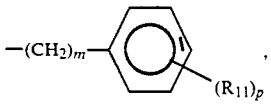

or the $R_{14}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_{21}$ is hydrogen, lower alkyl, cycloalkyl, phenyl or

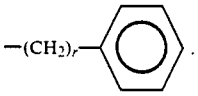

$R_{22}$ is hydrogen, lower alkyl,

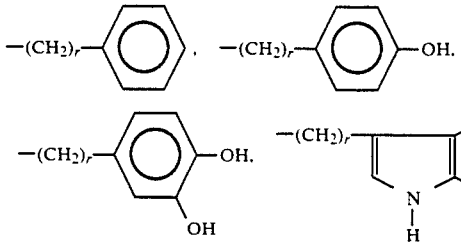

-continued

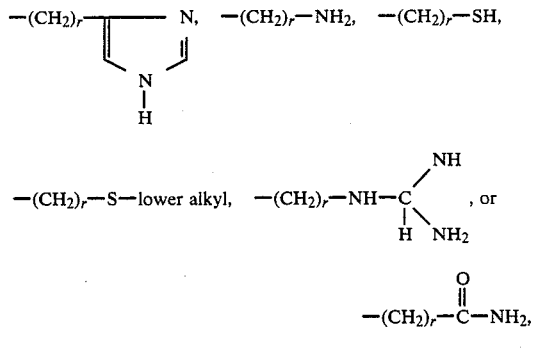

r is an integer from 1 to 4.

$R_1$ is alkyl of 1 to 10 carbons, aminoalkyl, haloalkyl,

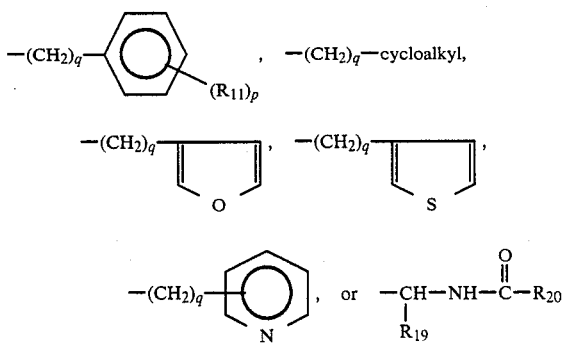

wherein q is zero or an integer from 1 to 7 and $R_{12}$ and p are as defined above.

$R_{19}$ and $R_{20}$ are independently selected from hydrogen, lower alkyl, halo substituted lower alkyl,

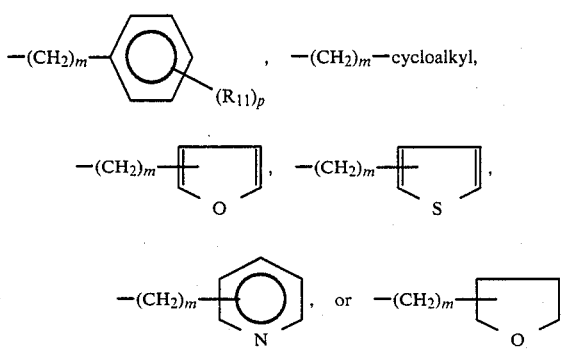

wherein m, $R_{11}$, and p are as defined above.

$R_2$ is hydrogen, lower alkyl, halo substituted lower alkyl,

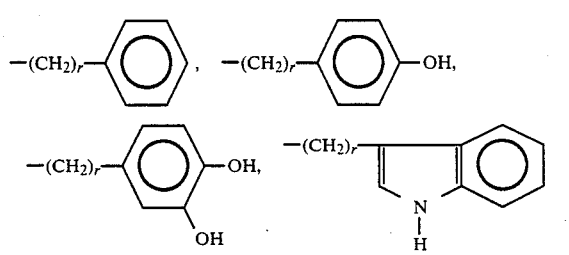

-continued

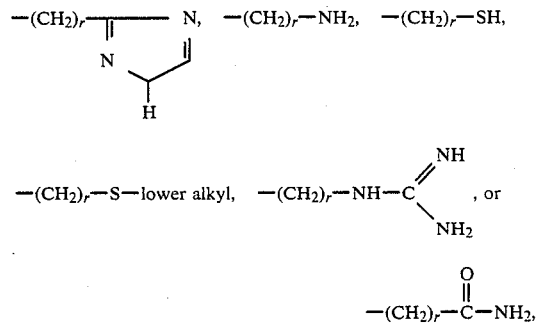

wherein r is as defined above.

$R_3$ and $R_6$ are independently selected from hydrogen, lower alkyl, benzyl, alkali metal such as Li, Na or K, benzhydryl, or

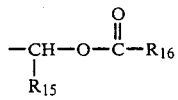

wherein $R_{15}$ is hydrogen, lower alkyl, cycloalkyl or phenyl, and $R_{16}$ is hydrogen, lower alkyl, lower alkoxy, phenyl, or $R_{15}$ and $R_{16}$ taken together are $—(CH_2)_2—$, $—(CH_2)_3—$, —CH=CH—, or

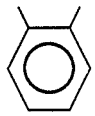

$R_{17}$ is lower alkyl, benzyl, or phenethyl.

$R_{18}$ is hydrogen, lower alkyl, benzyl or phenethyl.

This patent covers (S)-1-[6-amino-2-[[hydroxy(4-phenylbutyl)phosphinyl]oxy]-1-oxohexyl]-L-proline (SQ 29, 852).

U.S. Pat. No. 4, 248,883 to Sawayame et al discloses 1-(3-mercapto-2-methylpropanoyl)-prolyl amino acid derivatives of the formula

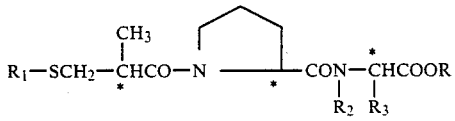

(I)

wherein R represents a hydrogen atom, a lower alkyl group, a phenyl-lower alkyl group or a substituted phenyl-lower alkyl group; $R_1$ represents a hydrogen atom, $R_4CO—$, $R_5S—$ or

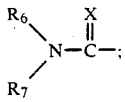

$R_2$ represents a hydrogen atom or a lower alkyl group;

$R_3$ represents a hydrogen atom, a phenyl group, a lower alkyl group, or a substituted lower alkyl group in which the substituent is hydroxy, phenyl-lower alkoxy, amino, guanidino, N-nitroguanidino, carboxyl, lower alkoxycarbonyl, phenyl-lower alkoxycarbonyl, carbamoyl, mercapto, lower alkylthio, phenyl, hydroxyphenyl, indolyl or imidazolyl; or $R_2$ and $R_3$ form a heterocyclic ring together with the nitrogen and carbon atoms to which they are respectively bonded; $R_4$ represents a lower alkyl group, a lower alkoxy group, a phenyl group, a substituted phenyl group, a phenyl-lower alkyl group, a substituted phenyl-lower alkyl group, a phenyl-lower alkoxy group, a substituted phenyl-lower alkoxy group, a phenoxy group, or a substituted phenoxy group; $R_5$ represents a lower alkyl group, a phenyl group, a substituted phenyl group, a phenyl-lower alkyl group, a substituted phenyl-lower alkyl group,

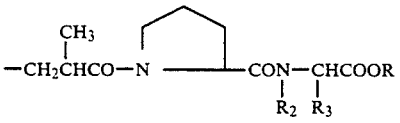

or an amino(-carboxy)lower alkyl group; $R_6$ represents a hydrogen atom or a lower alkyl group; $R_7$ represents a lower alkyl group, a phenyl group or a substituted phenyl group; X represents an oxygen or sulfur atom; and the substituent in the substituted phenyl group is a halogen atom, a lower alkyl group, or a lower alkoxy group; and salts of said derivatives.

U.S. Pat. No. 4,316,906 to Ondetti et al discloses ether and thioether mercaptoacyl prolines of the formula

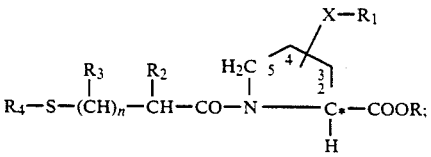

wherein the group X—$R_1$ is located at the 3- or 4-position in the ring;

X is oxygen or sulfur;

R is hydrogen or lower alkyl;

$R_1$ is lower alkyl, lower alkenyl, lower alkynyl, cycloalkyl, 1- or 2-adamantyl, aryl, substituted aryl, phenyl-lower alkylene or substituted phenyl-lower alkylene.

$R_2$ and $R_3$ are independently selected from hydrogen, lower alkyl, and trifluoromethyl;

$R_4$ is hydrogen, $R_5$—CO— or

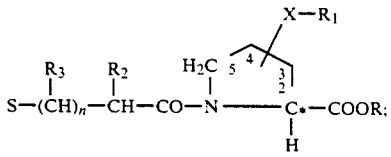

$R_5$ is lower alkyl, phenyl, phenyl-lower alkylene; substituted phenyl, or substituted phenyl-lower alkylene;

n is 0, 1 or 2; and salts thereof.

This Ondetti et al patent covers zofenopril

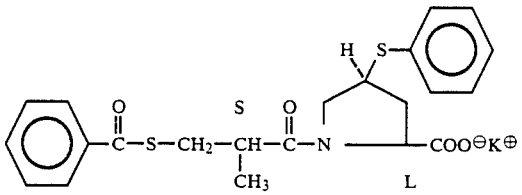

DESCRIPTION OF THE INVENTION

In accordance with the present invention, a method is provided for inhibiting onset of or treating migraine headaches wherein a therapeutically effective amount of an angiotensin converting enzyme inhibitor alone or in combination with a calcium channel blocker is systemically, such as orally or parenterally, administered over a prolonged period, whereby frequency and intensity of migraine headaches are significantly reduced.

Where a combination of ACE inhibitor and calcium channel blocker are to be used, the ACE inhibitor will be employed in a weight ratio to the calcium channel blocker of within the range of from about 0.1:1 to about 10:1 and preferably from about 0.4:1 to about 2.5:1.

The angiotensin converting enzyme inhibitor which may be employed herein includes substituted proline derivatives, such as any of those disclosed in U.S. Pat. No. 4,105,776 to Ondetti et al mentioned above, with captopril, that is, 1-[(2S)-3-mercapto-2-methylpropionyl]-L-proline, being preferred, carboxyalkyl dipeptide derivatives, such as any of those disclosed in European Patent Application No. 0 012 401 mentioned above, with N-(1-ethoxycarbonyl-3-phenylpropyl)-L-alanyl-L-proline, that is, enalapril, being preferred.

Other examples of angiotensin converting enzyme inhibitors suitable for use herein include any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline being preferred, phosphinylalkanoyl prolines disclosed in U.S. Pat. No. 4,168,267 mentioned above with fosinopril being preferred, mercaptoacyl derivatives of substituted prolines, disclosed in U.S. Pat. No. 4,316,906 with zofenopril being preferred, any of the phosphinylalkanoyl substituted prolines disclosed in U.S. Pat. No. 4,337,201 discussed above, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Pat. No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Pat. No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

The calcium antagonist which will be used herein may be diltiazem which is disclosed in U.S. Pat. No. 3,562,257 and which has the chemical name 3-(acetyloxy)-5-[2-(dimethylamino)ethyl-2,3-dihydro-2-(4-methoxyphenyl)-1,5-benzothiazepin-4(5H)-one and the structure

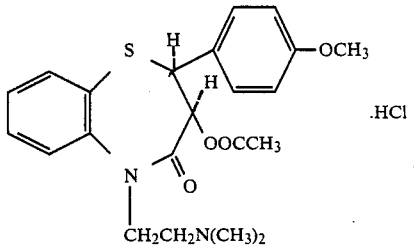

4-Phenyl-1,4-dihydropyridine calcium antagonists may be employed which will have the structure

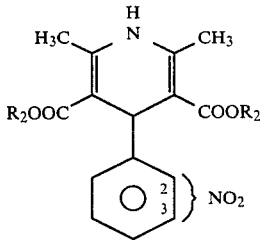

wherein $R_1$ and $R_2$ may be the same or different and are lower alkyl or lower alkoxy (lower alkyl) where lower alkyl and lower alkoxy contain 1 to 4 carbons.

The above compounds and methods for preparing same are disclosed in U.S. Pat. Nos. 3,644,627, 3,485,847, 3,488,359, 3,574,843, 3,799,934, 3,932,645 and 4,154,839 which are incorporated herein by reference.

The dihydropyridine calcium antagonist present in the composition of the invention will preferably by nifedipine, that is, the compound of formula C wherein $R_1$ $CH_3$, $R_2$ is $CH_3$ and $NO_2$ is at the 2-position, namely,

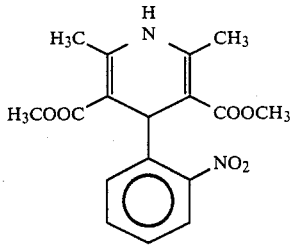

which is disclosed in U.S. Pat. Nos. 3,644,627 and 3,485,847.

Other preferred 4-phenyl-1,4-dihydropyridine calcium antagonists suitable for use herein include niludipine, that is, the compound of formula C wherein $R_1$ is $—(CH_2)_2OC_3H_7$, $R_2$ is $—(CH_2)_2OC_3H_7$ and $NO_2$ is at the 3-position (disclosed in U.S. Pat. Nos. 3,488,359 and 3,574,843); nimedipine, that is the compound of formula C wherein $R_1$ is $—(CH_2)_2OCH_3$, $R_2$ is $—CH(CH_3)_2$ and $NO_2$ is at the 3-position (disclosed in U.S. Pat. Nos. 3,799,934 and 3,932,645); nitrendipine, that is, the compound of formula C wherein $R_1$ is $—CH_2CH_3$, $R_2$ is $—CH_3$ and $NO_2$ is at the 3-position (disclosed in U.S. Pat. Nos. 3,799,934 and 3,932,645); and nisoldipine, that is, the compound of formula C wherein $R_1$ is $—CH_3$, $R_2$ is $—CH_2CH(CH_3)_2$ and $NO_2$ is at the 2-position (disclosed in U.S. Pat. Nos. 3,799,934, 3,932,645 and 4,154,839). Verapamil may also be employed.

The disclosure of the above-mentioned U.S. patents are incorporated herein by reference.

In carrying out the method of the present invention, the angiotensin converting enzyme inhibitor alone or in combination with the calcium channel blocker may be administered to mammalian species, such as monkeys, dogs, cats, rats and humans, and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms such as intramuscular, intraperitoneal, or intravenous are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.01 mg/kg to about 100 mg/kg and preferably from about 0.1 mg/kg to about 25 mg/kg alone or in combination with the calcium channel blocker in an amount within the range of from about 0.01 mg/kg to about 100 mg/kg and preferably from about 0.1 mg/kg to about 25 mg/kg with the ACE inhibitor and calcium channel blocker being employed together in the same oral dosage form or in separate oral dosage forms taken at the same time.

A preferred oral dosage form , such as tablets or capsules, will contain the ACE inhibitor in an amount of from about 0.1 to about 500 mg, preferably from about 125 to about 200 mg, and more preferably from about 25 to about 150 mg, alone or with the calcium channel blocker in an amount of from about 1 to about 350 mg, preferably from about 2 to about 200 mg, and more preferably from about 30 to about 150 mg.

For parenteral administration, the ACE inhibitor will be employed in an amount within the range of from about 0.005 mg/kg to about 10 mg/kg and preferably from about 0.01 mg/kg to about 1 mg/kg, alone or with the calcium channel blocker in an amount within the range of from about 0.005 mg/kg to about 20 mg/kg and preferably from about 0.01 mg/kg to about 2 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 50 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of ACE inhibitor and calcium channel blocker are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for onset of a migraine headache remains or the symptoms of a migraine headache continue. Sustained release forms of such formulations which may provide such amounts biweekly, weekly, monthly and the like may also be employed. A dosing period of at least two weeks and preferably at least 4 to 6 weeks are required to achieve minimal benefit.

The following Examples represent preferred embodiments of the present invention.

EXAMPLE 1

A captopril formulation suitable for oral administration in inhibiting onset of or treating a migraine headache is set out below.

1000 tablets each containing 25 mg of 1-[(2S)-3-mercapto-2-methylpropionyl]-L-proline were produced from the following ingredients.

| | |
|---|---|
| 1-[(2S)—3-Mercapto-2-methylpropionyl]-L-proline (captopril) | 25 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 25 mg of active ingredient which is used for inhibiting onset of or treating migraine headache.

EXAMPLE 2

By substituting 50 g of 1-(3-mercapto-2-D-methylpropanoyl)-L-proline for the captopril in Example 1, 1000 tablets each containing 50 mg of the 1-(3-mercapto-2-D-methylpropanoyl)-L-proline are produced which is useful in treating or inhibiting onset of migraine headache.

EXAMPLE 3

1000 tablets each containing 100 mg of captopril and 500 mg carbamazepine are produced from the following ingredients:

| | |
|---|---|
| Captopril | 100 g |
| Lactose | 100 g |
| Avicel | 150 g |
| Corn starch | 50 g |
| Magnesium stearate | 5 g |

The captopril, lactose and Avicel are admixed, then blended with the corn starch. Magnesium stearate is added. The dry mixture is compressed in a tablet press to form 1000 1205 mg tablets each containing 600 mg of active ingredients. The tablets are coated with a solution of Methocel E 15 (methyl cellulose) including as a color a lake containing yellow #6. The resulting tablets are useful in treating or inhibiting onset of migraine headache.

EXAMPLE 4

Two piece #1 gelatin capsules each containing 25 mg of captopril and 100 mg of carbamazepine are filled with a mixture of the following ingredients:

| | |
|---|---|
| Captopril | 25 mg |
| Magnesium stearate | 7 mg |
| USP lactose | 193 mg. |

The resulting capsules are useful in treating or inhibiting onset of migraine headache.

EXAMPLE 5

An injectable solution for use in treating or inhibiting onset of migraine headache trigeminal neuralgia is produced as follows:

| | |
|---|---|
| Captopril | 500 mg |
| Methyl paraben | 5 mg |
| Propyl paraben | 1 mg |
| Sodium chloride | 25 g |
| Water for injection qs. | 5 l. |

The captopril, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection for treating or inhibiting onset of migraine headache.

EXAMPLE 6

Tablets for use in treating or inhibiting onset of migraine headache are prepared as described in Example 1 except that N-(1-ethoxycarbonyl-3-phenylpropyl)-L-alanyl-L-proline (enalapril) is used in place of captopril.

EXAMPLE 7

An injectable for use in treating or inhibiting onset of migraine headache is prepared as described in Example 5 except that N-(1-ethoxycarbonyl-3-phenylpropyl)-L-alanyl-L-proline (enalapril) is employed in place of captopril.

EXAMPLE 8

A zofenopril formulation suitable for oral administration in treating or inhibiting onset of migraine headache is set out below.

1000 tablets each containing 100 mg of zofenopril are produced from the following ingredients.

| | |
|---|---|
| [1(S),4(S)]—1-[3-(benzoylthio)-2-methyl-1-oxopropyl-4-(phenylthio)-L-proline (zofenopril) | 100 g |
| Corn starch | 50 g |
| Gelatin | 7.5 g |
| Avicel (microcrystalline cellulose) | 25 g |
| Magnesium stearate | 2.5 g |

The zofenopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for treating or inhibiting onset of migraine headache.

EXAMPLE 9

By substituting 100 g of fosinopril for the zofenopril in Example 8, 1000 tablets each containing 100 mg of the fosinopril are produced which is useful in treating or inhibiting onset of migraine headache.

EXAMPLE 10

1000 tablets each containing 200 mg of fosinopril and 200 mg of carbamazepine are produced from the following ingredients:

| | |
|---|---|
| Fosinopril | 100 g |
| Lactose | 100 g |
| Avicel | 150 g |
| Corn starch | 50 g |
| Magnesium stearate | 5 g |

The fosinopril, carbamazepine, lactose and Avicel are admixed, then blended with the corn starch. Magnesium stearate is added. The dry mixture is compressed in a tablet press to form 1000 705 mg tablets each containing 300 mg of active ingredients. The tablets are coated with a solution of Methocel E 15 (methyl cellulose) including as a color a lake containing yellow #6. The resulting tablets are useful in treating or inhibiting onset of migraine headache.

EXAMPLE 11

Tablets for use in treating or inhibiting onset of migraine headache are prepared as described in Example 1 except that 1-[N-[hydroxy-(4-phenylbutyl)phosphinyl]-L-alanyl-L-proline, disodium salt (prepared as described in U.S. Pat. No. 4,432,971) is used in place of captopril.

EXAMPLE 12

An injectable for use in treating or inhibiting onset of migraine headache is prepared as described in Example 5 except that 1-[N-[hydroxy(4-phenylbutyl)phosphinyl]-L-alanyl]-L-proline, disodium salt (prepared as described in U.S. Pat. No. 4,432,971) is used in place of captopril.

EXAMPLE 13

A captopril-diltiazem formulation suitable for oral administration in the treatment of migraine headache is set out below.

1000 tablets each containing 100 mg of 1-[(2S)-3-mercapto-2-methylpropionyl]-L-proline and 100 mg of diltiazem are produced from the following ingredients:

| | |
|---|---|
| 1-(2S)—3-mercapto-2-methylpropionyl]-L-proline (captopril) | 100 g |
| Diltiazem | 100 g |
| Corn starch | 50 g |
| Gelatin | 7.5 g |
| Avicel (microcrystalline cellulose) | 25 g |
| Magnesium stearate | 2.5 g |

The captopril, diltiazem and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 200 mg of active ingredients which is used for preventing or treating migraine headache.

EXAMPLE 14

By substituting 100 g of 1-(3-mercapto-2-D-methylpropanoyl)-L-proline for the captopril in Example 13, 1000 tablets each containing 100 mg of the 1-(3-mercapto-2-D-methylpropanoyl)-L-proline and 100 mg diltiazem are produced which is useful in preventing or treating migraine headache.

EXAMPLE 15

1000 tablets each containing 200 mg of captopril and 200 mg nifedipine are produced from the following ingredients:

| | |
|---|---|
| Captopril | 200 g |
| Nifedipine | 200 g |
| Lactose | 100 g |
| Avicel | 150 g |
| Corn starch | 50 g |
| Magnesium stearate | 5 g |

The captopril, diltiazem, lactose and Avicel are admixed, then blended with the corn starch. Magnesium stearate is added. The dry mixture is compressed in a tablet press to form 1000 505 mg tablets each containing 200 mg of each active ingredient. The tablets are coated with a solution of Methocel E 15 (methyl cellulose) including as a color a lake containing yellow #6. The resulting tablets are useful in preventing or treating migraine headache.

EXAMPLE 16

Two piece #1 gelatin capsules each containing 250 mg of enalapril and 150 mg of nitrendipine are filled with a mixture of the following ingredients:

| | |
|---|---|
| Enalapril | 250 mg |
| Nitrendipine | 150 mg |
| Magnesium stearate | 7 mg |
| USP lactose | 193 mg |

The resulting capsules are useful in preventing or treating migraine headache.

EXAMPLE 17

An injectable solution for use in treating or preventing migraine headache is produced as follows:

| | |
|---|---|
| Captopril | 500 mg |
| Diltiazem | 300 mg |
| Methyl paraben | 5 g |
| Propyl paraben | 1 g |
| Sodium chloride | 25 g |
| Water for injection qs. | 5 L. |

The captopril, diltiazem, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 18

Tablets for use in preventing or treating migraine headache are prepared as described in Example 13 except that N-(1-ethoxycarbonyl-3-phenylpropyl)-L-alanyl-L-proline (enalapril) is used in place of captopril and nifedipine is used in place of diltiazem.

EXAMPLE 19

Tablets for use in treating or preventing migrane headache are prepared following the procedure of Example 13 except that zofenopril is employed in place of captopril and nisoldipine is used in place of diltiazem.

EXAMPLE 20

Tablets for use in treating or preventing migraine headache are prepared following the procedure of Example 13 except that fosinopril is employed in place of captopril.

EXAMPLE 21

Tablets for use in treating or preventing migraine headache are prepared following the procedure of Example 13 except that alacepril is employed in place of captopril.

EXAMPLE 22

Tablets for use in treating or preventing migraine headache are prepared following the procedure of Example 13 except that (S)-1-[6-amino-2-[[hydroxy-(4-phenylbutyl)phosphinyl]oxy]-1-oxohexyl]-L-proline or lisinopril is employed in place of captopril.

What is claimed is:

1. A method for inhibiting onset or treating migraine headache in a mammalian specie, which comprises administering to a mammalian specie in need of such treatment an effective amount of an angiotensin converting enzyme inhibitor alone or in combination with a calcium channel blocker over a prolonged period of treatment to reduce frequency and/or severity of migraine headaches during such period of treatment.

2. The method as defined in claim 1 wherein the angiotensin converting enzyme inhibitior is a phosphonate substituted amino or imino acid or salt thereof, a substituted proline derivative, a carboxyalkyl dipeptide derivative, a phosphinylalkanoyl proline derivative or a phosphonamidate derivative.

3. The method as defined in claim 1 wherein said angiotensin converting enzyme inhibitor alone or in combination with a calcium channel blocker is administered orally or parenterally.

4. The method as defined in claim 1 wherein said angiotensin converting enzyme inhibitor alone or in combination with a calcium channel blocker is admixed with a pharmaceutically acceptable carrier therefor.

5. The method as defined in claim 1 wherein said angiotensin converting enzyme inhibitor is a substituted proline derivative.

6. The method as defined in claim 1 wherein said angiotensin converting enzyme inhibitor is a carboxyalkyl dipeptide derivative.

7. The method as defined in claim 1 wherein said angiotensin converting enzyme inhibitor is a phosphinylalkanoyl proline derivative, a phosphoramidate derivative, or a phosphonate substituted amino or imino acid or salt thereof.

8. The method as defined in claim 1 wherein said angiotensin converting enzyme inhibitor is captopril which is optionally administered with a calcium channel blocker in single or separate dosage forms.

9. The method as defined in claim 1 wherein said angiotensin converting enzyme inhibitor is enalapril.

10. The method as defined in claim 1 wherein said angiotensin converting enzyme inhibitor is 1-[N-[hydroxy(4-phenylbutyl)-phosphinyl]-2-alanyl]-L-proline or its disodium salt.

11. The method as defined in claim 1 wherein said angiotensin converting enzyme inhibitor is administered in single or divided doses of from about 0.1 to about 500 mg/one to four times daily and where present the calcium channel blocker is administered in single or divided doses of from about 1 to about 300 mg/1 to 4 times daily.

12. The method as defined in claim 1 wherein said angiotensin converting enzyme inhibitor is captopril and is administered systemically in an amount of from about 0.1 to about 500 mg/1 to 4 times a day.

13. The method as defined in claim 1 wherein the angiotensin converting enzyme inhibitor is administered with a calcium channel blocker.

14. The method as defined in claim 13 wherein the calcium channel blocker is diltiazem or a 4-phenyl-1,4-dihydropyridine.

15. The method as defined in claim 14 wherein the 4-phenyl-1,4-dihydropyridine is nifedipine.

16. The method as defined in claim 13 wherein the angiotensin converting enzyme inhibitor is employed in a weight ratio to the calcium channel blocker of within the range of from about 0.1:1 to about 10:1.

* * * * *